United States Patent [19]

Ebert

[11] 4,223,325

[45] Sep. 16, 1980

[54] RECORDING DEVICE

[75] Inventor: Hans Ebert, Erlangen, Fed. Rep. of Germany

[73] Assignee: Siemens Aktiengesellschaft, Berlin & Munich, Fed. Rep. of Germany

[21] Appl. No.: 962,892

[22] Filed: Nov. 22, 1978

[30] Foreign Application Priority Data

Dec. 5, 1977 [DE] Fed. Rep. of Germany ....... 2754108

[51] Int. Cl.² ............................................ G01D 15/28
[52] U.S. Cl. .................................... 346/145; 346/136
[58] Field of Search ................. 346/145, 136, 68, 76 R

[56] References Cited

U.S. PATENT DOCUMENTS

| | | | |
|---|---|---|---|
| 3,082,970 | 3/1963 | Rasmussen | 346/136 X |
| 3,631,518 | 2/1969 | Battaglia | 346/145 |
| 3,946,406 | 3/1976 | Miura | 346/145 |

FOREIGN PATENT DOCUMENTS

| | | | |
|---|---|---|---|
| 1282989 | 11/1968 | Fed. Rep. of Germany. | |
| 845523 | 8/1960 | United Kingdom | 346/136 |

*Primary Examiner*—Joseph W. Hartary
*Attorney, Agent, or Firm*—Hill, Van Santen, Steadman, Chiara & Simpson

[57] ABSTRACT

A recording device for recording electrical signals on a moving strip or ribbon-shaped recording medium characterized by the device having a housing, which supports a drive means for rotating a feed roller, a writing needle and means for actuating the writing needle, and a carriage which is received in the housing and supports a supply of the recording medium, and at least one pressure roller. The carriage has a preformed part adjacent to the writing edge which conforms to the desired path for the medium as the carriage is inserted into the housing so that the insertion of the carriage into the housing places the recording medium automatically in the desired path around the writing edge and between the pressure and feed rollers.

11 Claims, 4 Drawing Figures

RECORDING DEVICE

BACKGROUND OF THE INVENTION

The present invention is directed to a recording device for recording electrical signals on a moving ribbon or tape-shaped recording medium. The device has a housing that contains a drive for a feed roller, at least one writing needle and means for actuating the needle in response to electrical signals. The housing receives a carriage, which supports a supply of the recording medium and has a pressure roller which coacts with the feed roller to feed the storage medium around the writing edge provided on the carrier for supporting the medium adjacent to the writing needle.

It is important, particularly with portable cardiographs, to provide a recording device for recording the physiological signals taken from the patient which recording device is a simple construction and is operationally reliable. Thus, it is desirable to provide a recording device which enables the desired operating qualities to be obtained. In particular, it is desirable that a carriage which supports a supply of the recording medium can be easily inserted into the housing of the device and does not require any extensive threading of the recording medium passed a writing edge.

SUMMARY OF THE INVENTION

The object of the present invention is to provide a recording device particularly useful for portable cardiographs which device is simple to use and operationally reliable. In particular, the device has a housing which receives the carriage that supports a supply of the recording medium and provides a writing edge to support the medium adjacent a needle. The carriage is designed in such a way that when the storage medium is looped around the writing edge, the insertion of the carriage into the housing automatically positions the recording medium in the position for recording without requiring any threading of the medium. To accomplish these tasks, a recording device having a housing which contains a drive means connected to a feed roller for the recording medium and supports at least one writing needle and means for actuating the needle in response to electrical signals, said device having a carriage for supporting a supply of recording medium being releasably inserted into the housing, said carriage providing a writing edge for supporting the recording medium at the writing needle as the writing needle writes thereon with the device having a plurality of guide rollers for guiding the recording medium and at least one pressure roller coacting with the feed roller to advance the recording medium has the improvements of the carriage supporting the pressure roller that coacts with the feed roller and being provided at one end with a performed part for supporting the writing edge, said performed part having a configuration that approximates the path of the recording medium as it is passed between the feed and pressure rollers and is engaged by the guide rollers, said carriage supporting at least one guide roller coacting with the writing edge to place the recording medium in the approximate position as the carriage is being inserted into the housing so that after insertion of the carriage into the housing, the recording medium is automatically disposed in the proper path around the writing edge and bertween the pressure and feed rollers.

In the carriage in accordance with the present invention, the travel path of the recording medium between all necessary feed, pressure and guide rollers is prescribed in its essential contours by the form of the performed part of the carriage. Therefore, the insertion of the carriage into the housing can be accomplished with only one hand which is a significant simplification of the operation. Since the recording medium is relatively firmly guided between the individual rollers, a dislocation of the recording medium after insertion of the carriage into the housing is practically impossible. Due to the optimally simple and reliable insertion of the carrier medium in the feed path, the optimum feed reliability is ensured during the recording process.

Preferably, the housing is provided with a pressure roller adjacent to the end of the writing needle and at least one of the pressure rollers of the housing or carriage is relativey movable in its mountings. The carriage also has spreading mass for applying pressure during insertion of the carriage to cause relative movement between the pressure and feed rollers and the spreading means is formed by said preformed part which acts as a spreading lever. Thus, when inserting the carriage the preformed front end or part of the carriage forces the pressure roller relative with respect to each other and to the feed roller so that recording medium which is loosely received on the writing edge when the carriage is removed from the housing is tightly moved into the desired path and squeezed firmly between the feed roller and the pressure roller of the carriage. The pressure roller of the carriage is mounted in horizontally extending slots provided in the carriage and is biased toward the feed roller and writing edge by spring elements disposed in the carriage. The pressure roller of the housing is mounted for movement in vertical slots. A portion of the preformed part or end of the carriage is provided with keyway means, which is formed by a recess adjacent and below the writing edge for receiving the axle of the pressure roller of the housing so that after insertion of the carriage, the recording medium has a looping angle around the writing edge of more than 180°. Such a provision reduces the contact surface of the writing needle on the recording medium, which minimizes the formation of branding or burn spots from the heated writing needle especially when using a thermosensitive recording medium. In so doing, the resolution of the quick developing, high frequency signal on the thermosensitive recording medium with a little feed time is improved.

In a further advantageous development of the invention, the carriage is provided with pins and the sidewalls of the housing are provided with slot means for receiving the pins and guiding the carriage during insertion into the housing. The slot means enable both translational rocking or swiveling movement of the carriage, respectively, in time succession. For locking the carriage in the operating position in the housing of the device, the housing is provided with a stop element which is pivotably mounted in the housing and biased by a spring into locking engagement with the carriage. Preferably, the stop extends across the width of the housing and is provided with a tab which can be engaged by a finger of the operator so that the stop can be unlocked by finger pressure. Upon the actuation or release of the stop, the entire carriage is automatically shifted to an upper position in which it can be grasped by the user due to a level which is mounted on the side of the housing and has one end extending through a slot into the housing to engage the carriage. The lever is biased around its point of mounting so that the engaged end lifts the carriage from the operating position.

The completion of the movement of the dipping motion, which is complicanted and is used to place the carriage into the operating position, is simplified by the invention. Because of the simple elemental movements that are now only needed, for example translation, rocking and reversal, the removal of the carriage by the user can also be carried out with a one hand manipulation. The good manipulaton qualities are an advantage particularly when the device is used as a recording device for a portable electrocardiograph which must be ready for operation as quick as possible in case of an emergency.

DESCRIPTION OF THE PREFERRED EMBODIMENT

Figure 1:
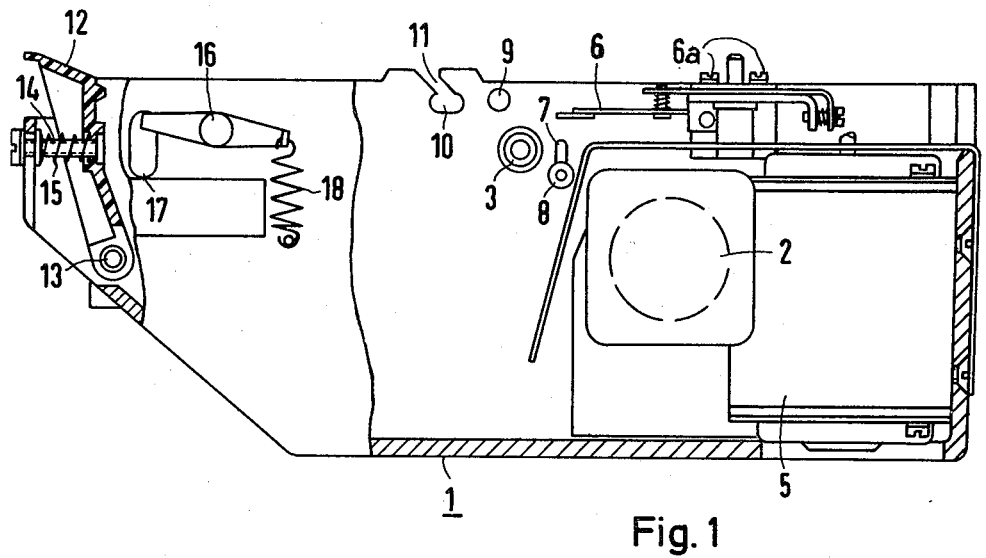
FIG. 1 is a side elevational view with portions broken away at each end of the housing of the recording device.
Figure 2:
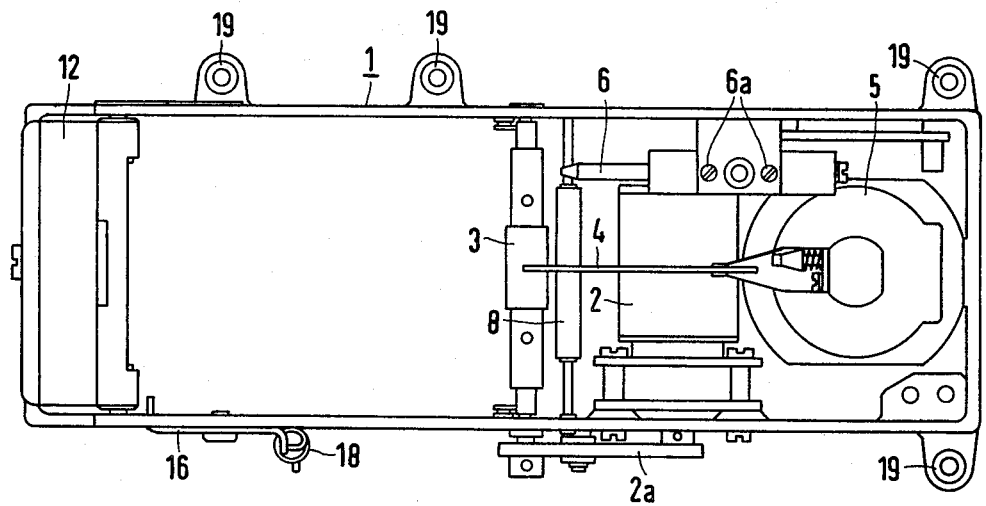
FIG. 2 is a plan top view of the housing illustrated in FIG. 1.
Figure 4:
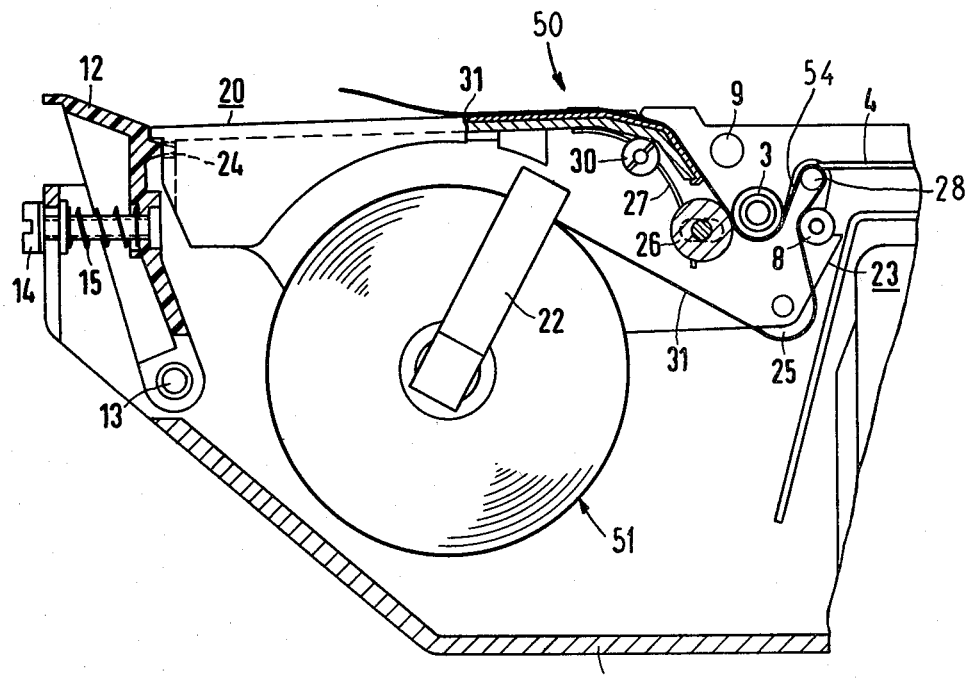
FIG. 4 is a partial cross-sectional view with portions in elevation for purposes of illustration of the carriage inserted in the housing.

The principles of the present invention are particularly useful in a recording device generally indicated at 50 in FIG. 4 which comprises a housing 1 and a carriage 20. The housing 1 is an elongated housing with dimensions of approximately 230 mm × 80 mm × 65 mm which has portions in the operating state, particularly those on the right hand side illustrated in FIGS. 1 and 2 covered by a cover plate (not illustrated). The height of the housing is essentially determined by the diameter of the roll of recording medium such as the roll 51 (FIG. 4). The width is determined also by the standard widths of the strip 31 or roll 51 of the recording medium to be used. In single channel recorders, a standard width of the recording medium is selected to be 50 or 60 mm. As illustrated in FIG. 1, the corner on the left hand side of the housing 1 is angled in order to save space.

The housing 1 receives and supports a drive means such as a drive motor 2 and supports a feed roller 3 which comprises a rigid shaft having an elastic rubber sleeve or roll of approximately 10 mm diameter arranged in the axial center thereof. The motor 2 drives the shaft of the feed roller 3 by means of a drive train such as the gear drive 2a (FIG. 2) or other equivalent means.

A writing needle 4, which is fixed to a signal receiving electromagnetic coil 5 which is a measuring element which actuates the needle in response to the electrical signal to be recorded, is mounted in the housing 1. In addition, a hand operated needle 6 for making designations on the recording medium is mounted in the housing above the drive motor 2 and, as illustrated, along one sidewall. The needle 6 is adjustable by means of adjustment screw 6a in such a manner that the designations can be applied to the outer edge of a standardized recording medium. Such an adjustment possibility is an advantage upon the utilization of the recording medium with varying standard widths. These components for the registration will not be further discussed in the following description.

A shaft 8 for a pressure roller is mounted for vertical movement in vertical slots 7 provided in the sidewall of housing 1 adjacent to the feed roller 3 and approximately under the end of the needle 4. The sidewalls also have slots or apertures 9 for receiving a cover to protect the recording parts which cover was mentioned hereinabove and, as illustrated, the slots 9 are positioned adjacent and above the feed roller 3. A recess 10 that runs horizontally is arranged in the housing 1 on both opposite sides to the left of the apertures or slots 9. The recesses extend to the upper free edge of the housing 1 by guide slits 11 that extend substantially diagonal. In this area, the sidewalls of the housing are provided with tongues or elevated portions that extend above the general height of the sidewalls to accept the diagonal slits 11. The slots 10 and 11 form slot means.

At the diagonal left hand end of the housing 1, a stop element 12, which is made of a plastic or other similar material is pivotably attached to extend across the entire width of the housing 1. This stop 12 is mounted for pivoting or rotational movement on an axle 13 and is biased by a means that includes a bolt 14 with a compression spring 15 into a seating position. As illustrated, the upper portion of the element 12 is provided with a tab which can be engaged by the operator's finger. Adjacent to the stop element 12, a lever 16 is pivotally mounted on one of the sidewalls and has one end bent to extend through a vertical slot 17 into the housing. The other end is engaged by a spring 18 so that the lever is rotatable in a clockwise direction with the end extending into the slot 17 urged in an upward direction. Adjacent the bottom surface of the housing, the housing is provided with a plurality of supports or lugs 19 (FIG. 2) which enable the housing to be attached to a base plate.

Figure 3:
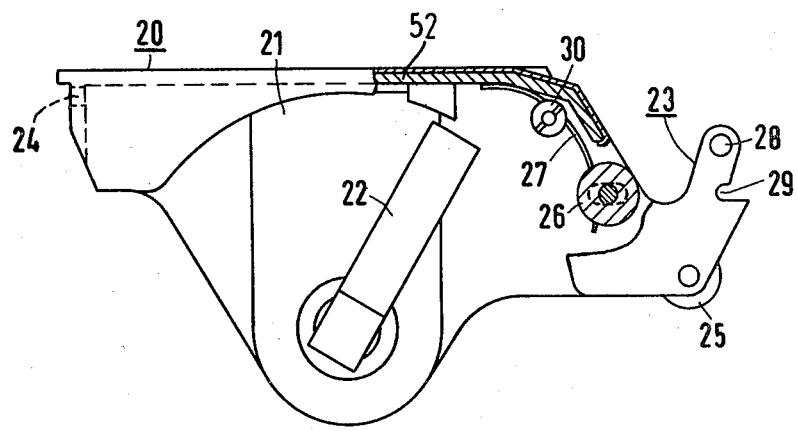
FIG. 3 is a side elevational view of the carriage with portions broken away for purposes of illustration in accordance with the present invention.

The carriage 20, as best illustrated in FIG. 3, has a flow table 52. Extending beneath the flow table 52 is a recording medium roll mounting element 21. When a roll 51 of the recording medium is received on the mounting element 21, it is guided laterally flush by means of a mechanism 22. As viewed in FIG. 3, the right hand portion of the paper flow table 52 of the carriage merges into an actual recording table which then extends into a preform part 23 which is offset from the flow table 52. The flow table 52 adjacent the left hand end is provided with a notch 24, which is engaged by the stop 12 to lock the carriage 20 in the housing 1 as illustrated in FIG. 4.

The front offset preformed part 23 of the carriage 20 rigidly supports a guide roller 25 adjacent the bottom portion and supports a shaft for a rubber pressure roller 26 in horizontally extending slots (illustrated in broken lines). The roller 26 is urged to the right by steel spring elements such as 27 and thus the slot and the spring functions as a spring bearing. A thin shaft 28 is arranged at the upper end of the preformed part 23 and forms the writing edge for supporting the recording medium as the needle 4 writes or inscribes thereon. Immediately below the writing edge formed by the shaft 28, the edge of the preform is provided with notches or recesses 29 which extend horizontally inward and form keyway means for receiving the vertically movable shaft of the pressure roller on insertion of the carriage 20 into the housing 1. The housing 1 also supports two linchpins or pins 30 which are received in the diagonal slots 11 that extend into the horizontal slots or recesses 10 and cooperate to hold the carriage in the housing 1.

The carriage 20 supports a roll 51 of the recording medium 31 which is drawn from the roll in the path 54 when the carriage is inserted in the housing. As illustrated in FIG. 4, the medium 31 extends around the guide roller 25, around the pressure roller 8 to loop around the writing guide or edge 28, then around the feed roller 3 and between the feed roller and the pressure roller 26 onto the forward end of the flow table 52.

In utilizing the device, after a roll 51 is placed on the roll support 21, a portion of the medium 31 is pulled and loosely looped around the guide roller 25, the writing edge 28 and has a leading end held on the flow table 52. While holding the entire carriage in one hand, it can be introduced into the housing by having the pins 30 inserted into the diagonal extending slits of the slot means with the carriage extending at an inclined angle of approximately 45° relative to the horizontal top edge of the housing 1. In this position and because of the inclination, the front offset preformed part 23 of the carriage 20 is positioned under the drive roller 3 in the housing 1. After the carriage 20 has been pushed forward so that the guide pins 30 are received in the recess 10, the carriage 20 is rotated in a counterclockwise direction around the axis of the pins 30 toward a horizontal position so that the feed roller 3 comes to lie between the two shafts of rollers 25 and 26 of the carriage 20. With the subsequent upward movement of the front offset preformed part 23 of the carrier 20, the shaft of roller 8 which is mounted for vertical movement in the vertically extending slots 7 is shifted upward in the slots 7. At the same time, the feed roller 3 presses the shaft of roller 26 against the springs 27 toward the left hand portion of its mounting slot so that the feed roller 3 and the counter pressure shaft or pressure roller 26 are firmly seated upon one another with the recording medium 31 guided and engaged therebetween. When the paper flow table 52 comes to lie almost horizontally upon the upper edge of the housing 1, it can still be moved in a horizontal direction in the horizontal recesses 10 of the housing 1 so that an exact seating of the roller 8 in the keyway means formed by the recess 29 can occur. The paper flow table 52 of the cage or carriage 20 is thereby moved against the pressure of the spring lever 16 until the prestressed stop element 12 engages in the notch 24. The entire carriage according to FIG. 3 is then rigidly locked in the horizontal position in the housing 1. In order to unlock the medium carriage 20, the stop 12 now need only be actuated by finger pressure. Due to the spring 18 acting on the lever 16, the carriage 20 is then tilted up so that the entire carriage 20 can now be taken out of the housing 1 by reversing the above mentioned steps.

By the arrangement of the shaft of pressure roller 8 in the keyway means 29, a back pressure on the recording medium 31 and therefore a looping angle of the recording medium 31 around the writing edge 28 of more than 180° is produced. Because of this and because of the spring pressure of the pressure roller 26, the recording medium is tauntly guided during its flow and the potential for the creation of a loose loop of the recording medium is decreased so that when recording upon thermosensitive material, the branding spot or burned spot on the recording medium 31 by the heated writing needle is minimized. Because of the size of the branding spot or mark of the heated writing needle 4, the resolving power upon recording is adversely affected, precisely in the case of a low or slow feed time of the recording medium. By means of the back pressure of the recording medium 31, the resolution upon recording of the quick developing, high frequency signal is improved by the same time.

To facilitate the manipulation during the operation of the recording device, it is important that the movable parts of the housing 1 with the feed roller for feeding the recording medium 31 and the carriage 20 be balanced in their dimensions with the magnitude of the effective spring forces. In the sample embodiment described, the pressure shaft 26 is stressed with a spring force of 2×100 p. The force of the coil springs 15 and 18 for locking and unlocking, respectively, lie approximately below the total value.

Although various minor modifications may be suggested by those versed in the art, it should be understood that I wish to embody within the scope of the patent warranted hereon, all such modifications as reasonably and properly come within the scope of my contribution to the art.

I claim:

1. In a recording device for recording electrical signals on a moving ribbon-shaped recording medium, said device having a housing, which contains a drive means connected to a feed roller for the recording medium and supports at least one writing needle and means for actuating said needle in response to the electrical signals, said device having a carriage for supporting a supply of the recording medium being releasably inserted into the housing, said carriage providing at least one writing edge for supporting and recording medium as the writing needle writes thereon, said device having a plurality of guide rollers for guiding the recording medium and at least one pressure roller coacting with the feed roller to advance the recording medium, the improvements comprising the housing supporting a first pressure roller adjacent to the end of the writing needle, the carriage supporting a second pressure roller and being provided at one end with a preformed part for supporting the writing edge between the feed roller and the first pressure roller, said preformed part having a configuration that approximates the path of the recording medium as it is passed between the feed and pressure rollers and is engaged by the guide rollers, said carriage supporting at least one guide roller coacting with the writing edge to place the recording medium in the approximate position as the carriage is being inserted into the housing so that after completion of the insertion of the carriage, the recording medium is automatically disposed in the proper path around the writing edge and between the pressure and feed rollers.

2. In a recording device according to claim 1, wherein at least one of the pressure rollers of the housing and carriage being mounted for relative movement, said carriage having spreading means for applying pressure during insertion of the carriage to cause relative movement between said pressure rollers and said feed roller, said spreading means being formed by said preformed part so that after insertion of the carriage with the recording medium looped around the writing edge, said pressure rollers moved to squeeze the recording medium between the feed roller and said pressure roller.

3. In a recording device according to claim 1, wherein the feed roller comprises a rigid shaft mounted in the housing, said shaft being connected to the drive means by a gear train, said shaft supporting an elastic roll on the center thereof.

4. In a recording device according to claim 1, wherein said carriage being provided with a pair of pins, said housing has a pair of parallel extending sides, each of said sides being provided with slot means for receiving said pins and guiding said carriage during insertion into the housing, said slot means having a lateral portion intersected by a sloping portion so that both the translational and rotational motions can occur.

5. In a recording device according to claim 4, wherein the sides of the housing adjacent said slot means are provided with raised tongue portions.

6. In a recording device according to claim 1, wherein said housing has a stop element pivotably mounted adjacent one end, means biasing said stop element into engagement with an end of said carriage for locking said carriage in said housing in the operational position.

7. In a recording device according to claim 6, wherein said stop element extends across the entire width of said housing and is provided with a tab engageable with a finger to move it from an engaged position to the disengaged position against said biasing means.

8. In a recording device according to claim 1, wherein a sidewall of said housing is provided with a lever mounted for rotation thereon, said lever having one end extending through a slot in said sidewall and being biased by a spring with said one end moving in an upward direction so that when the carriage is released from said housing, said spring lever urges it to a position enabling it to be grasped by the operator.

9. In a recording device for recording electrical signals on a moving ribbon-shaped recording medium, said device having a housing, which contains a drive means connected to a feed roller for the recording medium and supports at least one writing needle and means for actuating said needle in response to the electrical signals, said device having a carriage for supporting a supply of the recording medium being releasably inserted into the housing, said carriage providing at least one writing edge for supporting the recording medium as the writing needle writes thereon, said device having a plurality of guide rollers for guiding the recording medium and at least one pressure roller coacting with the feed roller to advance the recording medium, the improvements comprising the housing having one of the pressure rollers mounted adjacent to the end of the writing needle for relative movement in vertically extending slots, the carriage being provided at one end with a preformed part for supporting the writing edge and having a second of the pressure rollers being supported for relative movement in horizontally extending slots, a spring being disposed on the carriage and urging the second pressure roller toward the writing edge, said preformed part having a configuration that approximates the path of the recording medium as it is passed between the feed and pressure rollers and is engaged by the guide rollers, said preformed part forming spreading means for applying pressure during insertion of the carriage in the housing to cause relative movement between the pressure rollers and the feed roller and the movement of each of the pressure rollers in their respective slots, said carriage supporting at least one guide roller coacting with the writing edge to place the recording medium in the approximate position as the carriage is being inserted into the housing so that after completion of the insertion of the carriage, the recording medium is automatically disposed in the proper path around the writing edge and squeezed between the pressure and feed rollers.

10. In a recording device according to claim 9, wherein the preformed part of the carriage having keyway means for engaging an axle of the vertically displaceable pressure roller of the housing and holding it in a given position when the carriage is inserted in said housing, said keyway means being a recess along one edge of said preformed part.

11. In a recording device according to claim 10, wherein said recess is configured relative to the writing edge so that the vertically movable pressure roller of the housing and the feed roller coact with the writing edge to cause the medium to be moved through a loop greater than 180°.

* * * * *